United States Patent [19]

Stotts

[11] Patent Number: 4,741,342
[45] Date of Patent: May 3, 1988

[54] CARDIAC PACEMAKER WITH SELECTIVE UNIPOLAR/BIPOLAR PACING

[75] Inventor: Lawrence J. Stotts, Lake Jackson, Tex.

[73] Assignee: Intermedics, Inc., Angleton, Tex.

[21] Appl. No.: 838,603

[22] Filed: Mar. 11, 1986

[51] Int. Cl.$^4$ .............................................. A61N 1/36
[52] U.S. Cl. ........................ 128/419 P; 128/419 PG; 128/421
[58] Field of Search .............. 128/421, 419 P, 419 PG

[56] References Cited

U.S. PATENT DOCUMENTS

| | | | |
|---|---|---|---|
| 4,462,406 | 7/1984 | De Cote | 128/419 PG |
| 4,470,418 | 9/1984 | Herscovici et al. | 128/419 PG |
| 4,498,478 | 2/1985 | Bourgeois | 128/419 PG |
| 4,549,548 | 10/1985 | Wittkampf et al. | 128/419 PG |
| 4,558,702 | 12/1985 | Barreras et al. | 128/419 PG |
| 4,606,349 | 8/1986 | Livingston et al. | 128/419 PG |

Primary Examiner—William E. Kamm
Assistant Examiner—Timothy Keegan
Attorney, Agent, or Firm—Leitner, Greene & Christensen

[57] ABSTRACT

A dual chamber cardiac pacemaker is programmable for either unipolar or bipolar pacing of the atrium or the ventricle, independently of the pacing mode for the other chamber. Transistor switches are utilized for selectively connecting the various anodic electrodes to ground such that one of those electrodes is grounded at all times and isolation is maintained from circuit paths for non-selected modes. Switch control is effected using signals having the highest voltage level of proper polarity in the system, to assure maintenance of the selected switch states despite possible random voltages arising from external influences. Cumulative buildup of charge on coupling capacitors is prevented by selectively and actively discharging them after the respective chamber is paced.

5 Claims, 3 Drawing Sheets

CARDIAC PACEMAKER WITH SELECTIVE UNIPOLAR/BIPOLAR PACING

BACKGROUND OF THE INVENTION

1. Field of the Invention

The present invention relates generally to artificial cardiac pacing, and more particularly to cardiac pacemakers which are selectively adaptable to provide either unipolar or bipolar pacing of the patient's heart.

2. Prior Art

It is, of course, well known that the sinoatrial (S-A) node of the normal mammalian heart acts as the natural pacemaker by which rhythmic electrical excitation is developed and propagated to the atria. In response to this excitation, the atrial chambers contract, thereby pumping blood into the ventricles. The excitation is further propagated through the atrioventricular (A-V) node, which imposes a delay, and then via the conduction system consisting of the bundle of His and Purkinge fibers to the ventricular muscle, thereby causing contraction and the pumping of blood from the ventricles. Disruption of this natural pacing and propagation system occurs as a result of aging and/or disease.

Where normal rate or rhythm is not spontaneously maintained in the heart beat of a human patient, the condition is corrected typically by artifical pacing in which a cardiac pacemaker, selected according to the particular deficiency of the patient, is implanted. In its simplest form, an implantable cardiac pacemaker consists of a pulse generator (or stimulus generator) powered by a self-contained battery pack; and a lead assembly including an electrode adapted to be positioned in stimulating relationship with excitable myocardial tissue either externally (an epicardial electrode) or internally (an endocardial electrode) of the heart, and an insulated electrically conductive lead interconnecting the pulse generator and the tissue-stimulating electrode to deliver the electrical stimuli from the generator to the tissue via an electrical circuit completed by a second electrode and the body tissue and fluids. The electrical stimuli induce desired contractions of the respective chamber at a rate based on the timing of their delivery, the rate being appropriate for a normal sinus rhythm.

The entire lead assembly is often referred to simply as the lead, and the terminology "lead" and "electrode" are sometimes used interchangably, albeit inaccurately. For present purposes, the cardiac tissue-stimulating electrode which is placed in contact with or immediately adjacent the excitable cardiac tissue will be referred to as the stimulating cathodic electrode, or simply the cathode, and the other electrode will be referred to as the anodic electrode, or simply the anode. In fact, however, the coupling may be such that each electrode acts to a certain extent, at different times, as a cathode and an anode. In any event it is well known that activity takes place at both electrodes in the delivery of pacing stimuli. The customary lead choice for the cathode of the implantable cardiac pacemaker is an endocardial lead, because it is readily inserted pervenously into the chamber to be paced. In contrast, an epicardial lead requires thoracic surgery to affix the electrode to the heart. The pulse generator, which is housed with the battery and other circuitry in a conductive case, is typically placed in a subcutaneous pocket formed by an incision in the patient's chest.

Cardiac pacing may be achieved through anodal stimulation rather than cathodal stimulation. However, the stimulation threshold (that is, the minimum electrical impulse necessary to initiate contraction of the excitable cardiac tissue) for anodal stimulation is greater than the threshold achieved using cathodal stimulation. The explanation for this lies in the action of the polarizing force of the stimulating electric field on the ions along membranes of excitable myocardial cells subjected to the field. In essence, the highest current density and current flow exist at the side of each affected cell closest to the cathode. Thus, a cathodal pulse is depolarizing, or stimulating. In the case of anodal stimulation, however, the effect is hyperpolarizing, or nonstimulating. It is essential to the initiation of stimulation that field strength and duration be sufficient to maintain cell depolarization. This reduces the transmembrane potential to a level at which an action potential occurs, in turn spreading depolarization of adjacent cells and the consequent contraction of the tissue. Reduction of transmembrane potential occurs on the side of each affected cell furthest from the anode, and hence at a point of relatively lower field intensity, resulting in a higher threshold for anodal stimulation.

The pacing stimulation provided by the implanted cardiac pacemaker may be unipolar or bipolar, depending on the preference of the physician and the needs of the particular patient. For unipolar stimulation the anode is typically the metal case housing the pulse generator, and as such, is located remote from the heart. With a relatively small number of patients, current distribution to a large electrode in contact with the chest muscle may cause pectoral stimulation as the heart is paced. To avoid this, the conductive surface area of the case may be reduced by coating all but a small portion with non-conductive material, such as paraleen, which is inert to body fluids. This reduction in electrode area in turn reduces the effectiveness of the circuit's ground potential and creates some susceptibility to noise in the circuit.

For those reasons, the implanting physician may prefer to forego the simplicity of unipolar pacing in the case of a particularly sensitive patient, and choose instead to use bipolar pacing. For bipolar stimulation, the cathode and anode are located in relatively close proximity to each other. In a typical arrangement, the cathode is at the distal tip of the endocardial lead and the anode is a ring electrode insulated from the tip and spaced slightly back therefrom, say a half inch or so, on the same lead. Current flow is then between the tip and the ring, rather than the tip and the case. Of course, it is essential, if bipolar pacing is used, that the case be electrically isolated such that it is not a return path for current.

In the past, various schemes have been employed to permit selection of either unipolar or bipolar pacing with an implantable single chamber cardiac pacemaker. One of the earliest techniques employed transformers to isolate the pacing current from the case. However, a transformer fails to provide complete isolation in that the device couples to the conducting medium of the body via a magnetic field, rather than directly. Accordingly, some current will continue to flow through the patient's body during pacing, notwithstanding that its magnitude is smaller than would occur without the transformer. In addition to the possibility of pectoral stimulation, this shunt path for current effectively raises the stimulation threshold and therefore reduces battery life. Moreover, a transformer occupies considerably greater space (and thus increases the size of the implantable device) and is relatively more expensive, compared to other circuit components.

Subsequently, it was proposed that analog or solid state switches be used in techniques for selective unipolar or bipolar pacing and/or sensing. A serious problem encountered with solid state switches is susceptibility to random voltages in the system that can turn the switch on when it should be off, or vice versa. The control voltage for closing or opening the switch (that is, turning it on or off) must be reference to the switch and to the remainder of the circuit to avoid such occurrences.

An example of a prior art single chamber pacemaker configured for selective sensing in either unipolar mode or bipolar mode is found in U.S. Pat. No. 4,402,322. According to that patent, the pacemaker output circuit incorporates tri-state high current buffers and control logic which may be implemented in CMOS process technology, to provide various functions including combinations of unipolar or bipolar sensing. As described in that patent, however, the ring and tip electrodes are free to float in the bipolar mode because they are isolated from the power supply voltages and system ground. Such an arrangement suffers loss of control of the ground reference in the system, and the consequent possibility that a random voltage in the system can create an undesired current path, and hence, incomplete isolation.

These types of problems are magnified when it is sought to provide selective (programmable) bipolar or unipolar pacing for a dual chamber cardiac pacemaker. U.S. Pat. No. 4,462,406 describes an isolation system for a dual chamber pacemaker to reduce the possibility of crosstalk and cross-stimulation between bipolar leads in the atrium and the ventricle, where the leads share a common ground connection. According to that patent, crosstalk is characterized by a crossover of sensed signals in one channel (e.g., the bipolar lead in the atrium) to the other channel (e.g., the bipolar lead in the ventricle), and cross-stimulation is the analogous situation in the pacing mode. The patent describes an arrangement in which the atrial and ventricular leads are multiplexed by toggling a set of semiconductor switches at a high chopping rate and with break-before-make action such that at no instant of time are both channel lead pairs connected to the pacemaker. Inasmuch as one lead pair is always disconnected before the other is connected, there is an instant during each multiplexing cycle in which neither lead pair is connected to the ground, and hence, in which a portion of the system is floating and therefore susceptible to random switching or incomplete isolation. Also, that patent does not address selective unipolar/bipolar pacing in a dual chamber pacemaker.

In U.S. Pat. No. 4,558,702, a dual chamber cardiac pacemaker is provided with an input/output circuit responsive to a command signal to selectively operate in unipolar and bipolar pacing and sensing modes. The circuit of that patent utilizes three P-channel MOS transistor switches to permit selection of any of the four combinations of unipolar and bipolar pacing and sensing, that is, bipolar sensing with unipolar pacing, unipolar sensing with bipolar pacing, unipolar sensing with unipolar pacing, or bipolar sensing with bipolar pacing. However, there is no provision for selective mixed modes of unipolar and bipolar stimulation of the two chambers.

SUMMARY OF THE INVENTION

There is a need for a dual chamber cardiac pacemaker which is adaptable, through programming, to selectively utilize mixed modes of unipolar and bipolar pacing, and to do so with a switching technique that assures a virtual absence of susceptibility of the circuitry to uncontrolled or random switching. Accordingly, it is a principal object of the present invention to fulfill that need.

Briefly, according to the present invention, a control circuit is provided for a dual chamber cardiac pacemaker by which pacing current flow is selectively and completely controlled between five electrodes (namely atrial tip, atrial ring, ventricular tip, ventriclar ring, and pulse generator case or other reference electrode) to permit four distinct pacing modes in which both chambers may either undergo unipolar or bipolar stimulation, or either chamber may undergo unipolar stimulation while the other chamber undergoes bipolar stimulation. The control is exercised through a combination of switch configuration and switching control voltages such that the selected modes are completely isolated from one another and from the non-selected modes. That is to say, the arrangement assures that there will be no cross-stimulation between chambers, and that neither chamber will be subjected to the non-selected mode of stimulation.

In a preferred embodiment of the invention, three P-channel MOS (metal-oxide-silicon) switches are employed to limit the direction of stimulating current flow between the five electrodes, and the operation of the overall circuit is controlled in such a manner that when one or more of the switches is selected to be on (closed) or off (open), it or they remain(s) in that state unless and until the respective other state is selected, regardless of any random voltages or pacing voltages that may exist in the system at any given instant of time. P-channel switches are employed for isolation in the usual pacemaker situation where the positive terminal of the pacer supply is established as the ground reference (for reasons mentioned earlier concerning desirability of cathodal stimulation). These switches are used to selectively connect or disconnect the system ground among the electrodes, or more simply, for ground switching.

According to one important aspect of the invention, switching control is exercised such that at least one of the pacing electrodes is grounded at all times, or equivalently, at least one of the switches is always on. This means that the volume conductor comprising the body tissue and fluids is always grounded with reference to the pacemaker circuit. The particular electrode connected to ground in any given interval of time may be different from the electrode(s) connected to ground in the immediately preceding or succeeding interval so long as an electrode is always connected to the ground reference bus. In essence, the system is never allowed to float, and hence, the likelihood that any random voltage would cause unintended switching to occur is remote.

According to another important aspect of the invention, switching control is manifested using a voltage of greatest magnitude in the system, to assure that when a switch is intended to be off, it remains off until dictated otherwise by the control circuit.

Still another important aspect of the invention is the provision of an active discharge circuit to prevent a cumulative buildup of charge on capacitors as the pulse generator and output circuit cycles through its selected operation.

Accordingly, it is a further object of the invention to provide a dual chamber cardiac pacemaker which is selectively programmable to perform any combination of unipolar and bipolar stimulation of the two chambers.

Another object of the invention is to provide an output isolation circuit for a dual chamber cardiac pacemaker in which the system ground is selectively switched among the several anodic electrodes for selective unipolar or bipolar pacing of either chamber independently of the pacing mode selected for the other chamber, free of cross-stimulation.

Still another object of the invention is to provide an output isolation circuit for a dual chamber cardiac pacemaker in which semiconductor switches within the isolation circuit are selectively turned on and off under the control of a voltage having a magnitude higher than that of any controlled or random voltage that can or may occur within the pacemaker system, to assure switching control.

Yet another object of the invention is to provide a stimulus generator for a dual chamber cardiac pacemaker in which capacitors are actively discharged by controlled switching, to prevent cumulative voltage buildup.

BRIEF DESCRIPTION OF THE DRAWINGS

The above and other objects of the invention will become apparent to those of ordinary skill in the field to which the invention pertains, by reference to the accompanying detailed description of a preferred embodiment, taken in conjunction with the drawings in which.

DESCRIPTION OF THE PREFERRED EMBODIMENT

Figure 1:
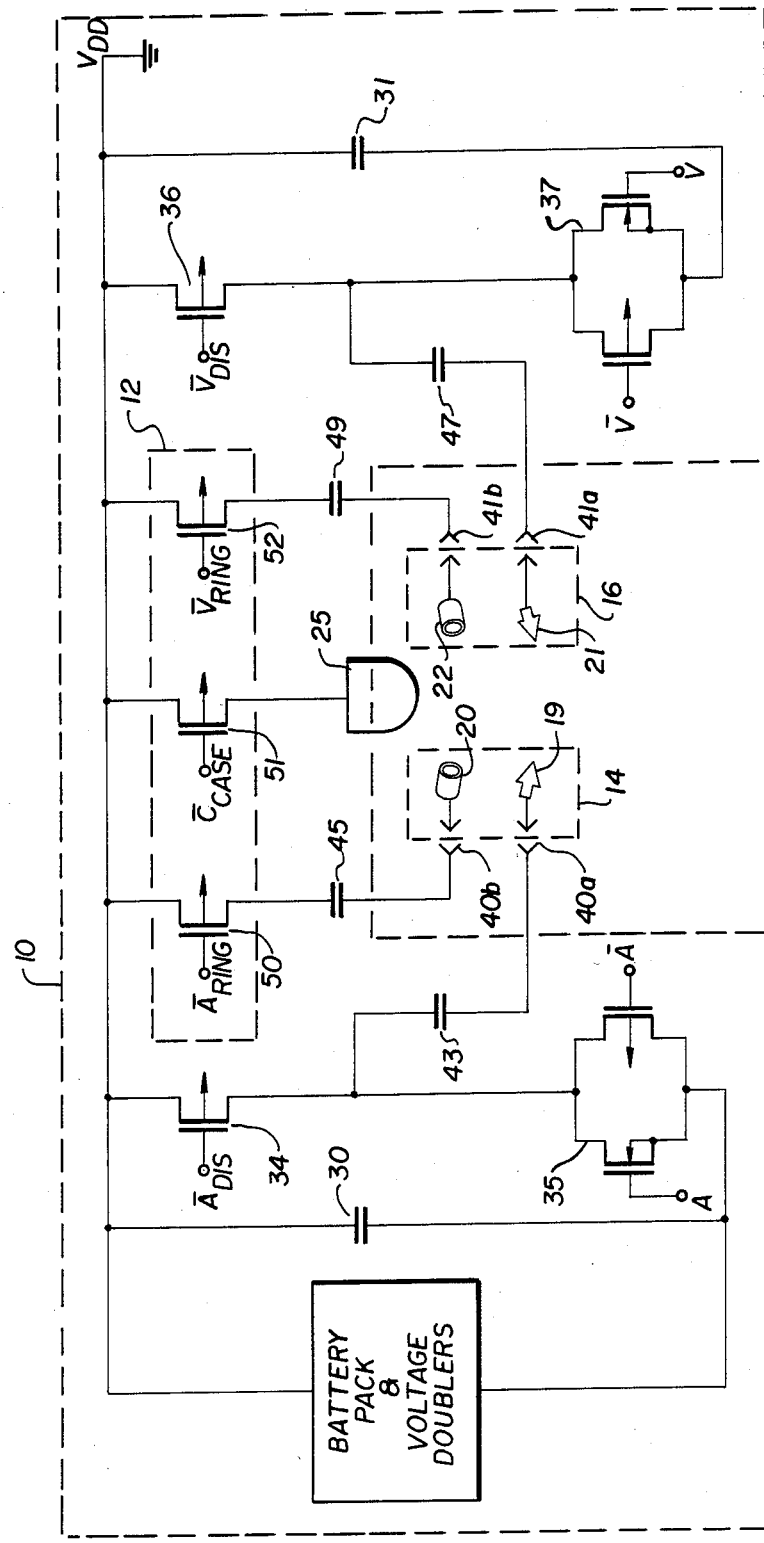
FIG. 1 is a simplified schematic diagram of a stimulus generator for a dual chamber cardiac pacemaker, having a unipolar/bipolar pacing isolation circuit according to the present invention.

Referring now to FIG. 1, the basic electrical circuit for a dual chamber cardiac pacemaker according to the present invention comprises a stimulus generator 10, which includes an output circuit or unipolar/bipolar pacing isolation circuit 12 and various essential components to be described below. Separate bipolar pacing lead assemblies represented by blocks 14 and 16 respectively, are adapted for placement in the atrium and the ventricle of the patient's heart.

In a conventional configuration, bipolar lead assembly 14 consists of a pair of conductors (typically, coils) in a flexible sheath inert to body fluids, the lead having male terminals at the proximal end for insertion into the female terminals of a lead connector integral with but electrically insulated from the case housing the stimulus generator. Details of such lead assemblies are well known and not critical to the invention, and hence, not shown in the drawings. In typical fashion for bipolar endocardial leads, an atrial lead, for example, terminates at the distal end in a cathode (tip) 19 and an anode (ring) 20 customarily configured as parts of a common electrode assembly. The electrode tip is adapted to be positioned in stimulating relationship with excitable myocardial tissue within the right atrial chamber. The anode ring is insulatively spaced one-half inch or so back from the tip in the electrode assembly of the lead. The ventricular bipolar lead assembly 16 is similarly structured, with cathode 21 and anode 22 at the distal end adapted to be inserted into the right ventricle. Often, some means of active or passive fixation (not shown) are provided adjacent the electrode assembly on the lead, for retention of the electrodes in the proper position for capture (stimulation) within the respective chamber.

For unipolar stimulation of excitable tissue in either chamber, the conductive case 25 in which the stimulus generator (typically referred to simply as the pulse generator), battery pack and other elements are housed, may be used as the anode. Alternatively, the entire case 25 may be coated with an inert insulator such as paraleen, except for a small region (or may have a small conductive button electrically connected thereto) for use as the anodic electrode. In FIG. 1, the case 25 is represented as a separate component, but it will be understood that in practice generator 10 is housed therein.

The patient's body tissue and fluid constitute a volume conductor through which current is conducted between the various electrodes of the implanted cardiac pacemaker, according to the relative voltages on the electrodes.

Stimulus generator 10 is powered by a DC source, a battery or battery pack, having an output voltage which would typically be boosted in the pacemaker by a multiplier (not shown) to an output voltage $+V_{DD}$. For dual chamber stimulation, capacitors 30 and 31 are coupled in parallel across the positive and negative terminals of the boosted voltage supply, for charging to the voltage therebetween. For reasons mentioned above regarding preference for cathodal stimulation, the positive supply bus $+V_{DD}$ is connected to ground or the point of reference potential for the circuit. The current-conducting (source-drain) paths of a P-channel MOS field effect transistor 34 and semiconductor T-gate 35 are connected in series across capacitor 30, and a corresponding arrangement exists for capacitor 31, with P-channel transistor 36 and T-gate 37. Atrial bipolar lead assembly 14 may be coupled at its proximal end to the stimulus generator circuit 10 via a connector 40. With that lead assembly connected, atrial tip (cathode) 19 is connected via male/female terminal pair 40a and through capacitor 43 to a node between transistor 34 and T-gate 35. Similarly, atrial ring (anode) 20 is connected via male/female terminal pair 40b either directly, or if desired, through a capacitor 45 to a terminal of isolation circuit 12. A corresponding circuit configuration exists for ventricular bipolar lead assembly 16. Ventricular tip (cathode) 21 is coupled to a node between P-channel transistor 36 and T-gate 37 via the male/female terminal pair 41a of connector 41 and capacitor 47, and ventricular ring (anode) 22 is coupled to isolation circuit 12 via the terminal pair 41b of the connector and, if desired, a capacitor 49. T-gates 35 and 37 are transmission gates comprising separate N- and P-channel transistors having their source-drain paths connected in parallel.

Isolation circuit 12 comprises three P-channel MOS field effect transistors 50, 51 and 52 respectively coupling atrial anode 20, case electrode 25, and ventricular anode 22 to the circuit ground ($V_{DD}$) depending upon the operational state of each of those transistors. As will subsequently become clear from the ensuing description, the control circuitry utilized for selectively switching the three anodes to ground via the three P-channel transistors is configured to prevent undesired switching as a result of pacing voltages or extraneous or random voltages arising from external influences. Each of transistors 50, 51 and 52 has a relatively low on impedance and a relatively high off impedance.

Before proceeding with a description of circuit operation, it will be useful to stress certain significant aspects of the invention. For dual chamber operation, the desire is to control current flow between the five electrodes 19, 20, 21, 22 and 25 while stimulating the atrium and ventricle in any selected (programmed) combination of unipolar and bipolar pacing. Hence, atrium-ventricle may be paced bipolar-bipolar, unipolar-bipolar, bipolar-unipolar, or unipolar-unipolar, whichever of those modes is preferred. If, for example, the pacemaker is programmed for unipolar pacing of the atrium and bipolar pacing of the ventricle (in the proper sequence, of course), current flow is out of the case via the body saline into the atrial tip electrode during atrial stimulation. Because the body is a conducting medium, current may flow out of the case (in this example) to any of the other four electrodes unless there is a high degree of electrical isolation between the electrode pair selected for the stimulation and the other electrodes. Accordingly, it is essential that an enabling electrical potential exist only between case 25 and atrial tip electrode 19 during unipolar atrial stimulation. Similarly, during the proper sequence for bipolar ventricular stimulation, current should flow only between ventricular ring 22 and tip 21 in that interval, with all other current paths open.

Toward that end, when the atrium is to be stimulated in the unipolar mode, P-channel transistor 51 is switched into saturation, thereby connecting case 25 to ground. At that time, T-gate 35 is on, and hence capacitor 30 discharges through the loop consisting of switch 51, case 25, body fluid, atrial tip 19, capacitor 43 and T-gate 35. During that interval, each of transistors 50 and 52 is maintained in the off state, and hence no current flows between either of anodes 20 and 22 and tip 19. The energy impulse stimulates the atrium into contraction, pumping blood therefrom into the ventricle. The discharge of capacitor 30 through the atrial chamber results in the buildup of a voltage on capacitor 43. If left unattended, this charge will lessen the energy impulse for atrial stimulation in the next cycle. To prevent that, transistor 34 is switched on and capacitor 43 is discharged via that path to ground.

Transistor 52 is turned on immediately prior to switching off of transistor 51. Hence, ventricular ring 22 is grounded before case electrode 25 is disconnected from ground. At the same time, T-gate 37 is turned on, and capacitor 31 discharges through the body volume conductor via ventricular ring 22 and tip 21. Excitable myocardial tissue in the ventricle is thereby stimulated to contract, and blood is pumped from that chamber through the pulmonary artery. The process is repetitive with switch 51 turned on just before switch 52 is turned off, and so forth.

A key aspect of the invention is that the system is never allowed to float, and this is accomplished by assuring that one of the three P-channel switches 50, 51 and 52 is always on. An anode (either 20, 22, or 25, depending upon which switch is on) is therefore connected to ground at all times. Moreover, the switching of the three P-channel transistors 50, 51 and 52 is controlled by the largest voltage in the system, greater than any stimulating voltage or random voltage, as will be described presently in conjunction with the circuit of FIG. 3. This precludes accidental switching of ground or isolation of all three anodes from ground.

The timing sequence for controlling the operation of transistors 34, 36, 50, 51 and 52, and T-gates 35 and 37, is illustrated by reference to the timing diagram of FIG. 2 in conjunction with the signals applied to the respective gate terminals as shown in FIG. 1, for each of the four possible mixed modes of atrial-ventricular stimulation.

Referring to those two figures, and more specifically at this point to FIG. 2, the sequence for the various pacing modes is as follows. When both the atrium and the ventricle are to undergo bipolar pacing, the atrial ring is connected to $V_{DD}$ (and the ventricular ring is disconnected from $V_{DD}$) except during the width of the ventricular pacing pulse. During the latter interval the situation is reversed, with the atrial ring disconnected and the ventricular ring connected to $V_{DD}$. This is shown by the $A_B V_B$ portion of the timing diagram. Voltage level $A_{ring}$ is applied to the gate of transistor 50. When that level is negative relative to $V_{DD}$, the transistor is on. At the instant the ventricle is to be stimulated, the $A_{ring}$ level switches transistor 50 off as the $V_{ring}$ voltage switches transistor 52 on. Thereafter, the $A_{DIS}$ voltage switches transistor 34 on momentarily (thereby discharging capacitor 43) over the interval controlled by V. When $V_{ring}$ goes high, transistor 52 is switched off, $A_{ring}$ goes low to switch on transistor 50 and $V_{DIS}$ turns on transistor 36 to bleed the residual charge from capacitor 47. Throughout operation in the $A_B V_B$ mode, the voltage $C_{case}$ is at a level to keep transistor 51 off.

It will be observed by further reference to the $A_B V_U$ (bipolar stimulation of the atrium and unipolar stimulation of the ventricle), mode portion of the timing diagram, that, here the conductive case is always connected to $V_{DD}$ except during the interval of atrial pacing, during which the atrial ring is connected to $V_{DD}$. Switching control within the circuit in this mode is readily apparent from the timing diagram, by analogy to the preceding description of operation in the $A_B V_B$ mode.

During unipolar pacing of the atrium and bipolar pacing of the ventricle ($A_U V_B$), the case is grounded at all times except during ventricular pacing, when the ventricular ring is grounded. When both chambers are subjected to unipolar pacing ($A_U V_U$), the case is grounded throughout. Here again, operation in either mode is apparent from the timing diagram and analogy to the $A_B V_B$ mode description.

Thus, the volume conductor (the body fluid and tissue) is always connected to the pacemaker circuit ground. The potentials of any "floating" nodes are consequently established at a voltage between the largest magnitude voltage ($-V_{LS}$), which is at a multiple of the supply (battery) voltage ($-V_{SS}$), and ground ($V_{DD}$). Because of this, no random voltage is effective to cause a switch which is off by virtue of the control voltages in the circuit (that is, selectively off) to be turned on; nor to cause a switch which is selectively on, to be turned off.

Figure 3:
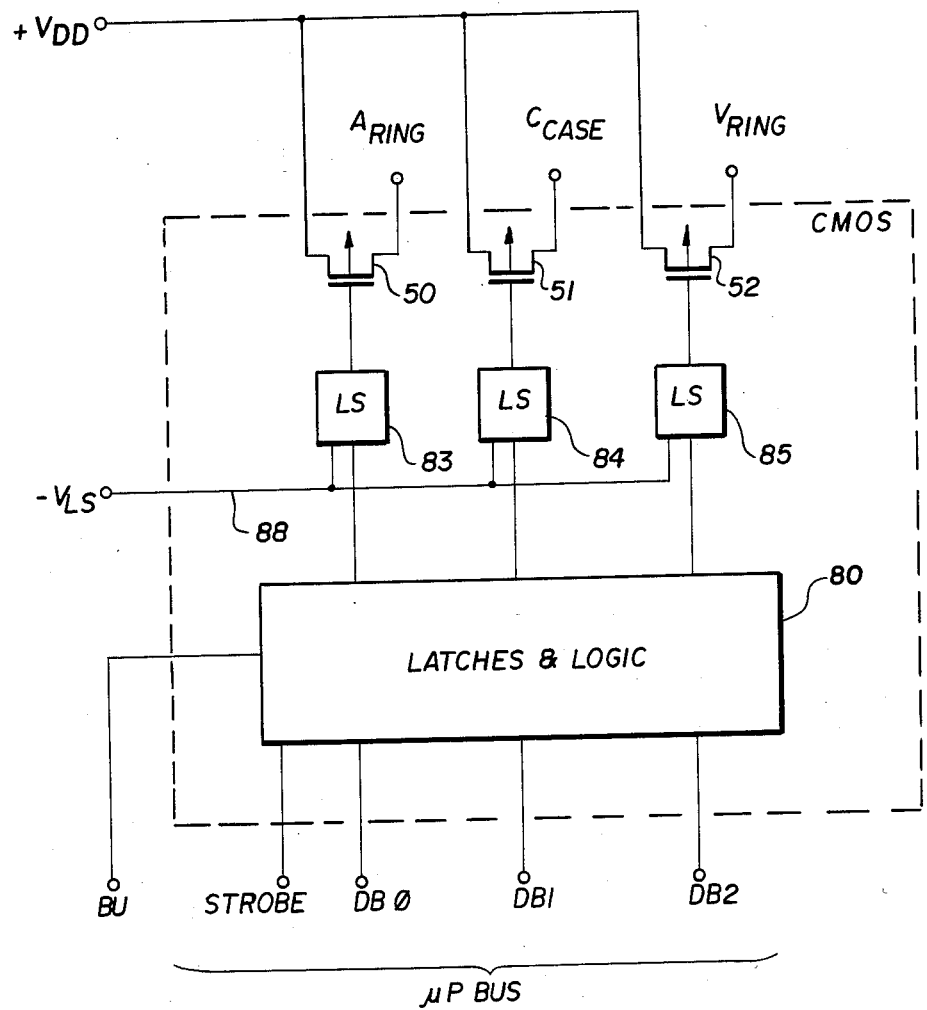
FIG. 3 is a circuit diagram of the control circuit for supplying signals according to the timing diagram of FIG. 2, to control the operation of the stimulus generator and output isolation circuit of FIG. 1.

A suitable logic circuit for controlling the isolation switches (transistors 50, 51 and 52 of FIG. 1) and advantageously fabricated in a CMOS integrated circuit chip incorporating those switches, is shown in FIG. 3. Each of transistors 50, 51 and 52 has its source electrode connected to $V_{DD}$ and its drain electrode connected to a respective anodic electrode (atrial ring, case and ventricular ring). The gate electrode of each transistor is coupled to the respective control signal outputs ($P_1$, $P_2$, $P_3$) of a latches and logic circuit 80, via respective level shifters 83, 84, 85. The level shifters are supplied a common operating voltage along path 88.

The latches and logic circuit 80 receives inputs from the microprocessor ($\mu$P), bus, including a timing strobe, and data bits DB0, DB1, DB2. A separate input BU will be explained presently.

The bootstrap supply ($-V_{LS}$) to the level shifters 83, 84, 85 is the most negative voltage in the pacemaker circuit. The level shifters thereby serve to keep the control signals from circuit 80 at a level sufficient to maintain the transistors 50, 51, 52 on when that state is desired. Hence, the shifters and bootstrap supply serve to reduce the on impedance and size of the switching transistors. With this arrangement, no signal can be developed within the pacemaker circuit at a higher (that is, more negative) level to turn on an isolation transistor designated to be off.

Figure 2:
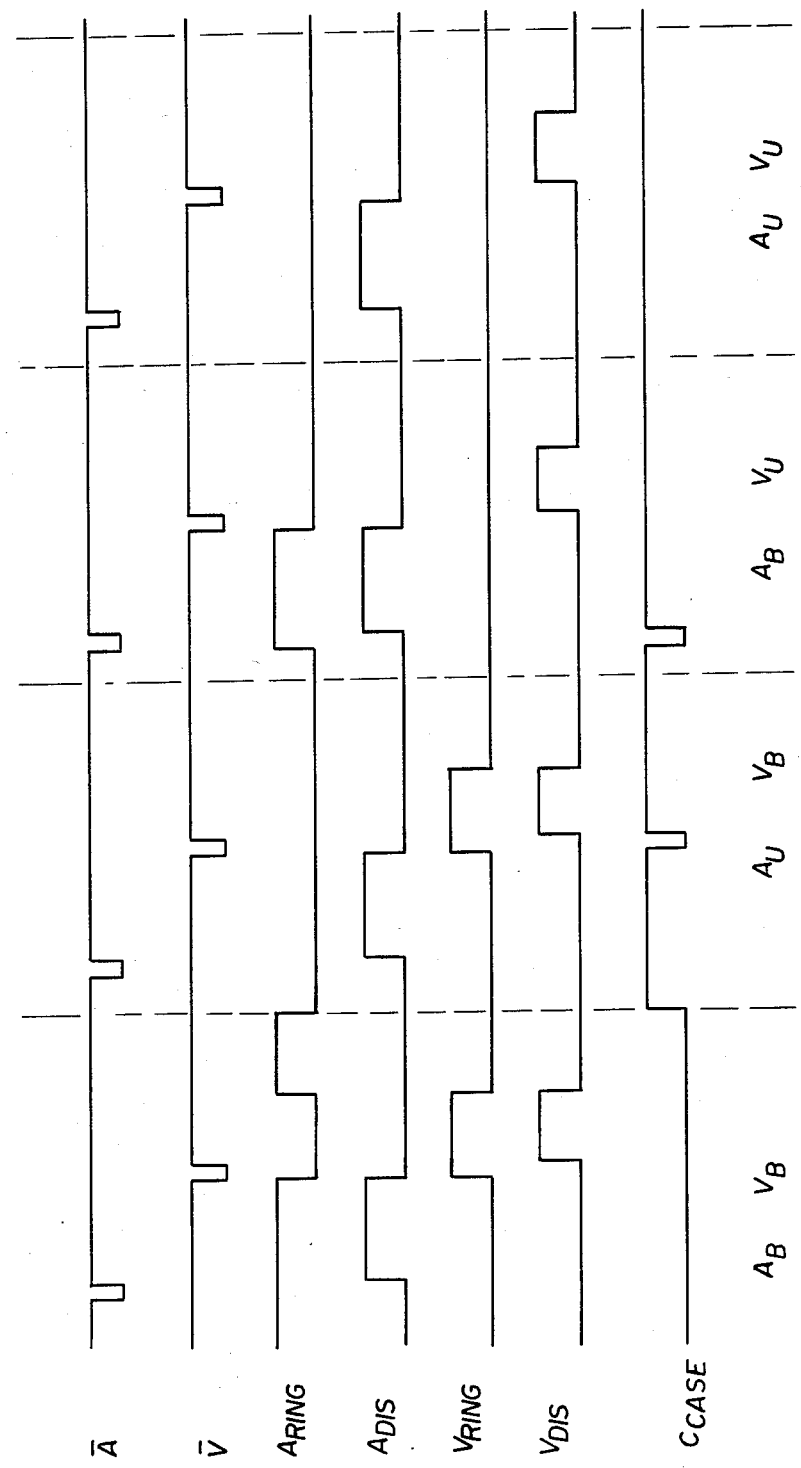
FIG. 2 is a timing diagram for controlling the circuit of FIG. 1, illustrating the timing sequence for the four possible modes of unipolar/bipolar pacing with the dual chamber pacemaker.

Circuit 80 latches the switch control data (DB0, DB1, DB2) from the $\mu$P bus, and provides the logic in accordance with the timing diagram of FIG. 2 to prevent all three of the isolation transistors from being off simultaneously. The backup (BU) input to circuit 80 sets the latches to override the $\mu$P bus data at any time that the switches, for whatever reason, are simultaneously in the "off" state. In essence, the BU input provides fail-safe operation. To that end, the latch setting by the BU signal puts the pacer in the unipolar stimulation mode in both chambers by latching the switches such that the case (and only the case, among the anodic electrodes) is grounded.

While a specific preferred embodiment of the invention has been described, variations will become apparent to those skilled in the field to which the invention pertains from the foregoing description and drawings. Accordingly, it is intended that the invention be limited only to the appended claims.

I claim:

1. A dual chamber cardiac pacemaker for pacing the atrial and ventricular chambers of the heart in any combination of unipolar and bipolar pacing modes, comprising:

atrial and ventricular leads each including a stimulating cathodic electrode and an anodic electrode to be positioned within the respective chamber of the heart.

a dc power source for delivering a voltage of predetermined polarity and magnitude between a power terminal and a ground reference terminal thereof, circuit means coupled across the power and reference terminals of said power source for sequentially applying said voltage as an electrical stimulus to first one and then the other of said stimulating electrodes, a case housing said circuit means, said case including a third anodic electrode, said circuit means including switch means for selectively conductively connecting at least one among the three anodic electrodes to the reference terminal of the power source at all times, and control means for completing a conductive path between the power terminal of the power source and the stimulating electrode for the respective chamber undergoing pacing while simultaneously actuating said switch means to maintain a conductive connection between the reference terminal of the power source and one of said anodic electrodes selected according to the desired pacing mode for said respective heart chamber undergoing pacing, said control means including means for selectively applying control voltages of the same polarity as the voltage at said power terminal to said switch means for actuation thereof to provide the respective conductive connections, and means for maintaining each of said control voltages at a magnitude greater than the magnitude of the voltage at said power terminal to maintain said switch means in the desired actuated state and to avoid undesired switching of said reference terminal among said anodic electrodes.

2. The pacemaker of claim 1, wherein:

said switch means includes first, second and third MOS transistor switches, each having a source-drain path and a gate, and each having its source-drain path connected between the reference terminal of said power source and a respective one of said three anodic electrodes, and said means for selectively applying control voltages to said switch means applies control voltages to the respective gates of said transistor switches for selective actuation thereof to render the respective source-drain path conductive according to which of said anodic electrodes is to be connected to said reference terminal at any given point in time.

3. In a dual chamber cardiac pacemaker adapted for selective stimulation of the atrial and ventricular chambers of the heart of a pacemaker patient in any combination of unipolar and bipolar pacing modes; said pacemaker including a case, a pulse generator housed in the case, a connector with terminals affixed to the case for electrically coupling a pair of lead assemblies, each including a stimulating cathodic electrode and an anodic electrode for introduction into a respective chamber of the patient's heart, to the pulse generator for delivery of voltage pulses of predetermined polarity and magnitude from the generator to the respective electrodes relative to a ground reference terminal of the generator, said case having an anodic electrode for electrical contact with the body tissue and fluid of the pacemaker patient when the pacemaker is implanted; an improved output isolation circuit comprising:

three semiconductor switch means each having relatively low on resistance and relatively high off resistance, and each connected at one side to the ground reference terminal of the pulse generator and respectively connected at the other side to the connector terminals for the anodic electrodes of said pair of lead assemblies and to said anodic electrode of the case, for electrical connection of each of said anodic electrodes to said ground reference terminal through a respective one of said switch means when in the on state, first and second means for selectively delivering the voltage pulses of said pulse generator to the connector terminals for the stimulating cathodic electrodes of said pair of lead assemblies, for sequential stimulation of the atrial and ventricular chambers, and means for selectively actuating each of said switch means to the on and off states to electrically connect at least one of said anodic electrodes to the ground reference terminal at all times, and, during selective delivery of any given one of said voltage pulses to the connector terminals, to electrically connect to the ground reference terminal one of said anodic electrodes applicable to the pacing mode selected for the heart chamber then undergoing stimulation, said means for selectively actuating each of said switch means including means for applying control voltages of predetermined magnitude and the same polarity as said voltage pulses to each of said switch means, and means for maintaining each of the control voltages at a magnitude exceeding the magnitude of said voltage pulses.

4. The improved output isolation circuit of a dual chamber cardiac pacemaker according to claim 3, wherein each of said first and second means for selectively delivering includes a coupling capacitor, and further including means for discharging residual charge on each said coupling capacitor after each stimulation cycle of the respective chamber.

5. A stimulus generator for an implantable cardiac pacemaker adapted to pace both chambers of one side of the heart via atrial and ventricular leads each having a cathode and an anode, and to do so with unipolar or bipolar stimulation of either chamber independently of the mode of stimulation of the other chamber, said stimulus generator comprising:

a first pair of terminals for respectively connecting said generator to the anode and cathode of the atrial lead and a second pair of terminals for respectively connecting said generator to the anode and cathode of the ventricular lead, means for sequential delivery of electrical stimuli from said generator to said first and second pairs of terminals, means establishing a point of ground potential for said generator, means for housing said generator, said housing means having integral therewith an anode for making contact with the body saline of a patient, three semiconductor switches each actuable separately to an "on" state and an "off" state, and each having a pair of electrodes establishing a low resistance conduction path therethrough when the respective switch is actuated to the "on" state, one of said electrodes of all three of said switches being connected to said point of ground potential and the other of said electrodes of each of said switches being respectively connected to said anode connection terminal for the atrial lead, said anode connection terminal for the ventricular lead, and said anode integral with the housing means, and means for selectively and independently actuating each of said three semiconductor switches for maintaining at least one of said switches in the "on" state at any given time during operation of the stimulus generator, including means for applying control voltages of predetermined magnitude and the same polarity as said electrical stimuli to each of said switches, and means for maintaining each of the control voltages at a magnitude exceeding the magnitude of said electrical stimuli.

* * * * *